United States Patent [19]

Hommann

[11] Patent Number: 5,442,827
[45] Date of Patent: Aug. 22, 1995

[54] ELECTRIC TOOTHBRUSH

[75] Inventor: Edgar Hommann, Grossaffoltern, Switzerland

[73] Assignee: Bausch & Lomb Incorporated, Rochester, N.Y.

[21] Appl. No.: 138,787

[22] Filed: Oct. 19, 1993

[51] Int. Cl.6 .................. A61C 17/34; A46B 13/02
[52] U.S. Cl. ........................................... 15/22.1; 74/70
[58] Field of Search ................. 15/22.1, 22.2, 22.4; 74/25, 26, 49, 70, 74

[56] References Cited

U.S. PATENT DOCUMENTS 4,603,448  8/1986  Middleton et al. ............... 15/22.1
5,077,855  1/1992  Ambasz ............................ 15/22.1

FOREIGN PATENT DOCUMENTS 0357863  3/1990  European Pat. Off. .
3544256  6/1987  Germany .......................... 15/22.1
8911427  11/1989  Germany .
3931982  4/1991  Germany .......................... 15/22.1

Primary Examiner—Edward L. Roberts, Jr.
Attorney, Agent, or Firm—Salvatore P. Pace; Katherine McGuire

[57] ABSTRACT

A handle component (1) of an electric toothbrush protrudes from the end of a hollow shaft (3), which holds a drive shaft (9) coaxially therein. A brush attachment (4) with rotatable bristle tufts (6) is disposed in the hollow shaft (3) in such a way that the drive shaft (9) is coupled with a shaft (7) in the brush attachment (4), wherein said shaft (7) drives the bristle tufts (6). The hollow shaft (3) is driven by a motor to oscillate around its longitudinal axis and/or to slide back and forth in the direction of its longitudinal axis. (FIG. 1)

3 Claims, 2 Drawing Sheets

ELECTRIC TOOTHBRUSH

BACKGROUND OF THE INVENTION

The invention relates to an electric toothbrush with a hand-held handle component, with a motor and drive mechanism, and a brush attachment, which has several rotatable tufts of bristles, fastened to said handle component. Said tufts are driven by a transmission built into said brush attachment. The drive mechanism is designed in such a way that, in addition to a rotational movement of the bristle tufts, it also creates an oscillating movement of the brush attachment about its longitudinal axis.

Such a toothbrush is the subject of U.S. Pat. No. 4,989,287 which issued on Feb. 5, 1991 and is of common ownership with the present application, and which is incorporated herein by reference. In this known toothbrush, the brush attachment can be oscillated about its longitudinal axis by means of a secure coupling link with which it is attached to the forward part of the handle component's casing. The transmission mechanism is designed as a non-rotating connecting rod within the brush attachment, wherein said connecting rod can create an oscillating movement about its longitudinal axis and a back-and-forth movement in the direction of its longitudinal axis by means of an oscillating crank and an eccentric that engages said crank. The back-and-forth movement of the connecting rod is transformed in the bristle head of the brush attachment to a rotational movement of the bristle tufts while the oscillating movement of the connecting rod creates a corresponding oscillation of the entire brush attachment.

Movement of the bristle tufts by means of a connecting rod is relatively expensive, and the connecting rod presents a problem if one wants to increase the angle at which the individual bristle tufts oscillate. Further, it is impossible to continuously rotate the bristle tufts in one rotational direction using a connecting rod.

Electric toothbrushes have also become known in which the bristle tufts are driven by a shaft instead of a connecting rod. U.S. Pat. No. 2,215,031 and DE-A-34 06 112 are examples of this state of the art. However, in both of these toothbrushes, the part that holds the bristle tufts of the toothbrush cannot be moved by the motor of the toothbrush relative to the handle component.

OBJECTS AND ADVANTAGES

The invention addresses the problem of designing a toothbrush of the type mentioned above wherein the bristle tufts can oscillate over a large angle or even complete a full rotation, and wherein the entire brush attachment that holds the bristle tufts can be moved by a motion relative to the handle component.

SUMMARY OF THE INVENTION

The invention solves this problem by designing the transmission mechanism which moves the bristle tufts of the brush head as a revolving shaft, while the brush attachment is designed to be removably fixed to a hollow shaft that can rotate and/or slide within the handle component. A drive shaft, which is located within said hollow shaft, is driven by a drive mechanism and removably couples with the shaft in the brush attachment. The drive mechanism is operable to simultaneously rotate the drive shaft and create an oscillating movement of the hollow shaft around its longitudinal axis and/or a back-and-forth movement in the direction of its longitudinal axis.

Since, according to the invention, the brush attachment is not inserted into the casing but onto a hollow shaft, and since the drive shaft for the shaft of the brush attachment is placed inside the hollow shaft, the brush attachment can be moved by driving the hollow shaft, without thereby affecting the drive of the bristle tufts. The toothbrush of the invention can be assembled relatively simply, and the movement of the brush attachment cleans teeth better than an electric toothbrush in which only the bristle tufts rotate. Driving the bristle tufts with a shaft makes it possible for said bristle tufts to rotate either continuously or to oscillate back and forth over a large angle.

The mechanism for moving the hollow shaft and the drive shaft can be designed in different ways. A particularly simple solution in which the hollow shaft rotates around its longitudinal axis, is to equip the hollow shaft within the handle component with a radial arm with a radially aligned crank guide, into which locks a toothbrush-motor driven eccentric, which is aligned parallel to the axis of the hollow shaft, and wherein said hollow shaft also has a toothed quadrant with external teeth into which meshes a toothed wheel that is rotatably mounted within the toothbrush, and wherein said toothed wheel in turn engages a pinion on the drive mechanism by means of another toothed wheel which is placed coaxially to said toothed wheel and connected to it to be rotationally rigid.

In such a toothbrush, the hollow shaft, which oscillates around its longitudinal axis, drives the drive shaft placed inside of it. The bristle tufts, therefore, change their rotational direction in the same cadence at which the brush attachment oscillates around its longitudinal axis.

In an alternate design, in which the hollow shaft is arranged to be rotatable and axially movable, the drive mechanism has a toothed wheel, designed as a bevel or contrate gear, which is driven by the pinion of the motor. The toothed wheel turns, perpendicularly to the main extension of the handle component, around the central axis of the of the bevel gear. The toothed wheel engages with an eccentric pin, which is aligned in parallel to its central axle, and a notch of an oscillating crank, which is connected to said hollow shaft parallel to the axis. The toothed wheel, which is designed as a bevel wheel or contrate gear, on the side that lies opposite to the side of the pinion of the motor, meshes with a pinion of the drive shaft.

In such a toothbrush, the individual tufts of bristles rotate continuously in one direction. The design of the mechanism in the brush attachment can be such that, for instance, the bristle tufts on one side rotate in the opposite direction to those on the other side. Simultaneously with the rotational motion of the bristle tufts, the brush attachment executes an elliptical movement because of the axially sliding and simultaneous oscillating movement of the hollow shaft around its longitudinal axis. Such a design is very advantageous for the teeth-cleaning process.

The combined movement of the hollow shaft and the drive shaft can be achieved easily by placing a crosshead, which can rotate on the eccentric pin, into the notch of the oscillating crank, and by designing the two sides of the crosshead which are parallel to the longitudinal axis of the toothbrush and/or the two corresponding sides of the notch to be curved or canted to allow the oscillating crank to perform a rocking motion. Such a mechanism corresponds largely to the previously mentioned '287 patent but differs from it, aside from its hollow shaft, primarily in that the toothed wheel with the eccentric simultaneously drives the drive shaft within the hollow shaft.

BRIEF DESCRIPTION OF THE DRAWINGS

The invention lends itself to many designs. To further explain its basic principle, two designs are illustrated in the drawing and described below. The drawing shows.

DETAILED DESCRIPTION

Figure 1:
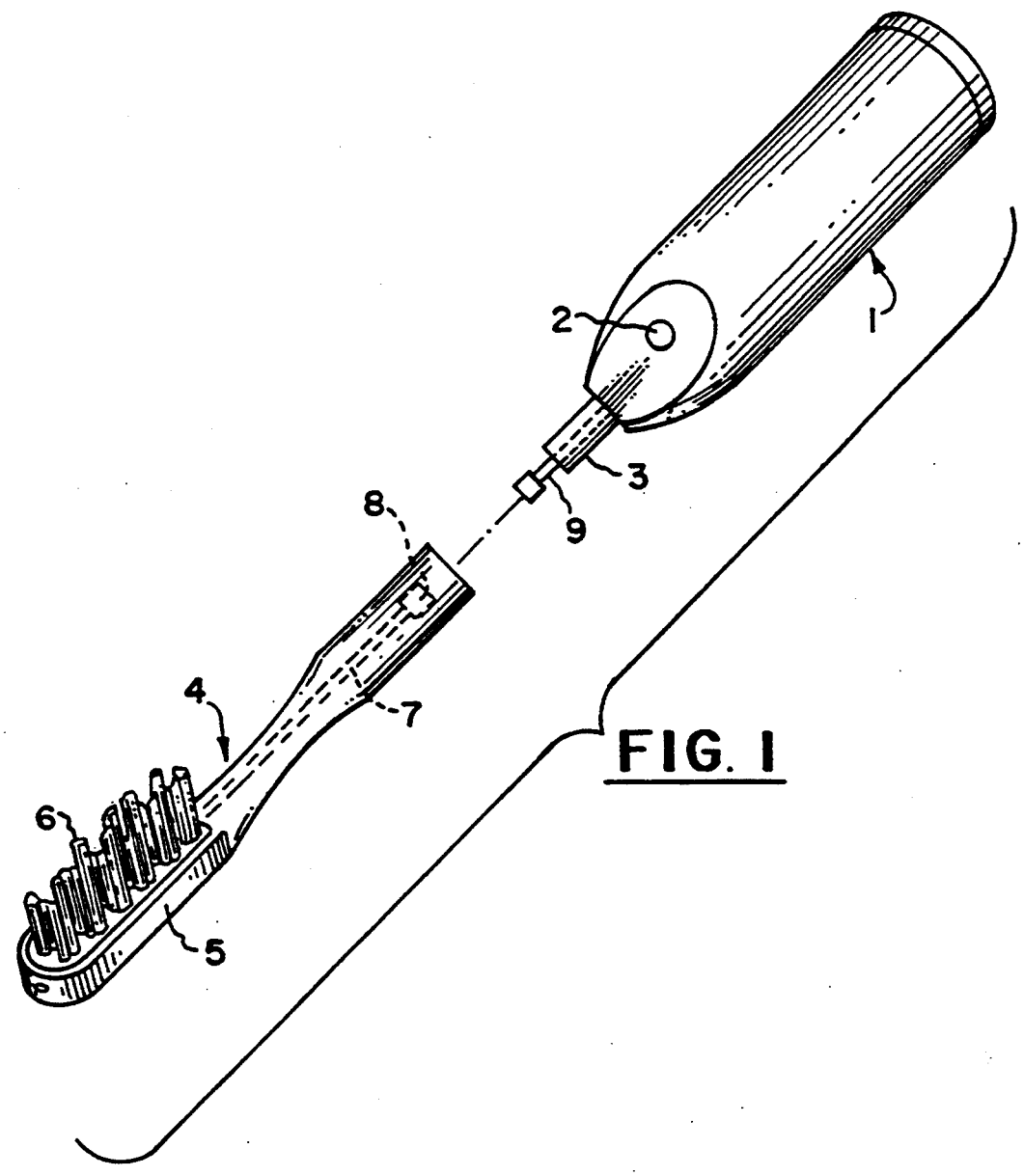
FIG. 1 a perspective view of a toothbrush according to the invention.

FIG. 1 shows in perspective a still unassembled electric toothbrush with a hand-held handle component 1 having a switch 2 to turn the electric toothbrush on and off. A hollow shaft 3 protrudes from the handle component 1 over which the brush attachment 4 is placed. When attached, the brush attachment is securely held on the hollow shaft 3 by a locking device (not shown).

The brush attachment 4 has a bristle head 5 with several rotatable bristle tufts 6. To drive the bristle tufts 6, a revolving shaft 7 is disposed within the brush attachment (shown by broken lines). Shaft 7 can be coupled to a drive shaft 9 by a coupler 8 which is arranged coaxially with the hollow shaft 3 in the handle component 1.

Depending on the type of toothbrush, the drive shaft 9 can rotate continuously or oscillate. Consequently, the bristle tufts 6 either rotate in one direction or they oscillate back and forth. The hollow shaft 3 is driven in such a way that it either oscillates around its longitudinal axis, slides back and forth in the direction of its longitudinal axis, or executes both movements simultaneously.

Figure 2:
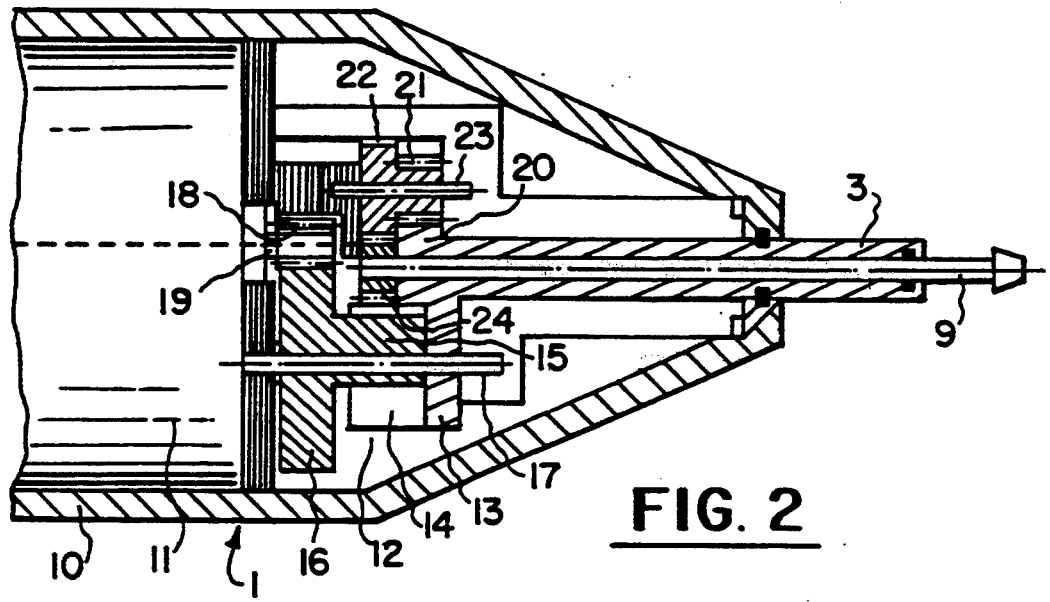
FIG. 2 a longitudinal cross-sectional view through an area of the mechanism of one design of the toothbrush.

FIG. 2 shows the front part Of the handle component 1, enlarged compared to FIG. 1, having a casing 10 which holds an electric motor 11 and a drive mechanism 12. The hollow shaft 3 and the drive shaft 9 again protrude from the casing 10.

Within the casing 10, the hollow shaft has a radially aligned arm 13 with a radially-extending crank guide 14. Crank guide 14 is engaged by an eccentric 15, which is placed at the front end of a toothed wheel 16, which is rotatably mounted on an axle 17, secured to the casing 10 parallel to the longitudinal axis of the handle component 1. Toothed wheel 16 engages a motor shaft 19, driven by motor 11, with a pinion 18. Because of the rotational movement of eccentric 15, the arm 13 oscillates constantly back and forth, so that the hollow shaft 3 executes a corresponding oscillating movement about its longitudinal axis.

On the side radially opposite to arm 13, the hollow shaft 3 has a toothed quadrant 20 into which meshes a toothed wheel 21 which, together with a rotationally rigidly connected toothed wheel 22, is rotatably mounted on a rigid-casing axle 23. Axle 23 is aligned parallel to the longitudinal axis of the handle component 1. The toothed wheel 22 engages a pinion 24 which sits within the casing 10 at the end of the drive shaft 9 which protrudes out of the hollow shaft 3. Because of the oscillating movement of the hollow shaft 3 created by the eccentric 15, the drive shaft 9, via the toothed quadrant 20, the toothed wheels 21, 22 and the pinion 24, consequently also oscillates about its longitudinal axis.

Figure 3:
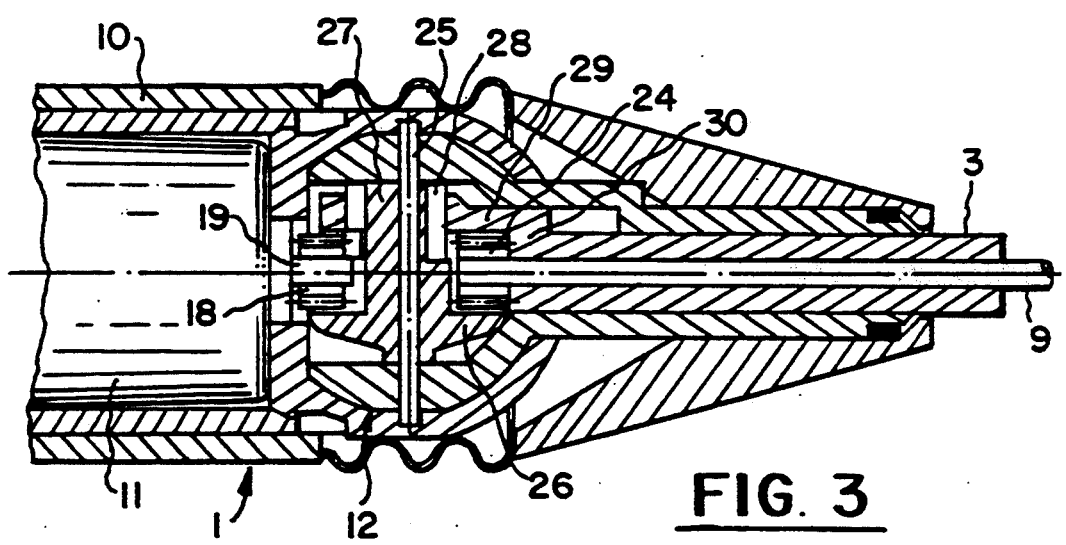
FIG. 3 a longitudinal cross-sectional view through an area of the mechanism of another design of the toothbrush.

FIG. 3 shows a design of the mechanism 12 that differs from that of FIG. 2, wherein the hollow shaft 3 and the drive shaft 9 are driven by the motor 11. The motor 11 in turn has a motor shaft 19 with a pinion 18. Pinion 18 continuously drives a toothed wheel 26 mounted rotatably around a rigid-casing axle 25. Toothed wheel 26 may be designed as a bevel gear or contrate gear. Axle 25 is rigidly mounted to the casing and aligned perpendicular to the longitudinal axis of the handle component 1. Toothed wheel 26, on the side that lies opposite to the side of pinion 18, meshes with the pinion 24, which drives the drive shaft 9. In this manner the drive shaft 9 rotates constantly in one direction.

An eccentric pin 27 is provided on the toothed wheel 26, extending in the direction of the axle 25, which engages a crosshead 28 of an oscillating crank 29. The oscillating crank 29 lies parallel to the hollow shaft 3 and is firmly connected thereto by a radial connecting link 30. The exact design of this component of the mechanism 12, including the toothed wheel 26, the eccentric pin 27, the crosshead 28 and the oscillating crank 29, is described in the '287 patent disclosure.

The hollow shaft 3 in the design shown in FIG. 3 is mounted in the casing 10 of the handle component 1 in such a way that it is rotatable and axially movable. Through the rotation of the eccentric pin 27, the hollow shaft 3 first slides back and forth in the direction of its longitudinal axis. However, since the eccentric pin 27 is mounted perpendicular to the hollow shaft 3 and since the hollow shaft 3 cannot move laterally, the oscillating crank 29 follows the lateral movement of the eccentric pin 27 by tilting around the longitudinal axis of the hollow shaft 3. This movement is also described in detail in the '287 patent disclosure. Thus, the hollow shaft 3 in this design executes a back and forth movement in longitudinal direction and also an oscillating movement around its longitudinal axis.

| List of Reference Numbers Used |
| --- |
| 1 handle component |
| 2 switch |
| 3 hollow shaft |
| 4 brush attachment |
| 5 brush head |
| 6 bristle tufts |
| 7 shaft |
| 8 coupler |
| 9 drive shaft |
| 10 casing |
| 11 motor |
| 12 drive mechanism |
| 13 arm |
| 14 crank guide |
| 15 eccentric |
| 16 toothed wheel |
| 17 axle |
| 18 pinion |
| 19 motor shaft |
| 20 toothed quadrant |
| 21 toothed wheel |
| 22 toothed wheel |
| 23 axle |
| 24 pinion |
| 25 revolving axle |
| 26 toothed wheel |

| -continued |
| --- |
| List of Reference Numbers Used |
| 27 eccentric pin |
| 28 crosshead |
| 29 oscillating crank |
| 30 connecting link |

I claim:

1. An electric toothbrush comprising:
   a) a hand-held handle component having a longitudinal axis and containing a motor having a rotating drive shaft and an inner shaft telescopingly and coaxially positioned within an outer shaft, said inner and outer shafts extending exteriorly from said handle component;
   b) gear means having first and second operating portions interconnecting said motor drive shaft with said outer and inner shafts, respectively, said gear means being operable to transmit the rotational movement of said motor drive shaft to simultaneous yet discrete oscillating movements of said outer and inner shafts about their common longitudinal axis;
   c) a brush head having an outer casing, a brush head shaft disposed within said casing, and at least one bristle tuft connected to and individually movable by said brush head shaft, said brush head being connected to said handle component such that said outer casing is frictionally engaged to and rotationally movable with said outer shaft, said handle inner shaft colinearly and rotationally fixed to said brush head shaft whereby said oscillating movement of said handle portion inner shaft causes a corresponding oscillating movement of said brush head shaft which ultimately moves said at least one bristle tuft;
   wherein said first operating portion of said gear means which moves said outer shaft comprises:
   i) a first pinion gear mounted to and rotatable with said motor drive shaft about a first axis which lies parallel to said longitudinal axis of said handle component;
   ii) a first toothed gear positioned in meshing engagement with said first pinion gear, said first toothed gear being rotatable about a second axis which lies spaced and parallel to said first axis;
   iii) an eccentric fixedly attached to and rotatable with said first toothed gear; and
   iv) a radially extending crank guide fixedly attached to said outer shaft so as to be movable therewith, said crank guide and said eccentric being coupled such that rotation of said eccentric causes said oscillating movement of said crank guide and said outer shaft.

2. The electric toothbrush of claim 1 wherein said outer and inner shafts each have proximal and distal ends located interiorly and exteriorly of said handle component, respectively, and wherein said second operating portion of said gear means which moves said inner shaft comprises:
   a) a second pinion gear fixedly secured to and rotatable with said inner shaft proximal end;
   b) a toothed quadrant fixed to and rotatable with said outer shaft proximal end on the side thereof opposite said crank guide; and
   c) a second toothed gear rotatably mounted in said handle component about a third axis which lies spaced and parallel to said first and second axes, said second toothed gear having first and second coaxial toothed surfaces lying in spaced, parallel planes, said first and second toothed surfaces positioned in meshing engagement with said toothed quadrant and said second pinion gear, respectively, whereby said oscillating movement of said outer shaft and, consequently, said toothed quadrant causes a corresponding oscillating movement of said inner shaft through said second toothed gear.

3. The electric toothbrush of claim 2 and further comprising a radial arm fixedly secured to and radially extending from said outer shaft proximal end opposite said toothed quadrant, said crank guide being fixedly secured to and movable with said radial arm.

* * * * *